United States Patent
Tsai et al.

(10) Patent No.: US 10,487,135 B2
(45) Date of Patent: Nov. 26, 2019

(54) METHOD FOR PREPARING LOW ENDOTOXIN COLLAGEN

(71) Applicant: Guangdong Victory Biotech Co., Ltd., Guangdong (CN)

(72) Inventors: Chen-Chih Tsai, Kinmen County (TW); Kuan-Yen Tung, Kinmen County (TW)

(73) Assignee: GUANGDONG VICTORY BIOTECH CO., INC., Guangdong Province (CN)

( * ) Notice: Subject to any disclaimer, the term of this patent is extended or adjusted under 35 U.S.C. 154(b) by 34 days.

(21) Appl. No.: 15/871,969

(22) Filed: Jan. 15, 2018

(65) Prior Publication Data

US 2019/0055303 A1 Feb. 21, 2019

(30) Foreign Application Priority Data

Aug. 17, 2017 (CN) .......................... 2017 1 0706991

(51) Int. Cl.
*C07K 14/78* (2006.01)
*C12P 21/06* (2006.01)

(52) U.S. Cl.
CPC .............. *C07K 14/78* (2013.01); *C12P 21/06* (2013.01)

(58) Field of Classification Search
CPC .................................. C07K 14/78; C12P 21/06
USPC .......................................................... 435/68.1
See application file for complete search history.

(56) References Cited

U.S. PATENT DOCUMENTS 5,138,030 A * 8/1992 Pachence .................. A23J 1/10
530/356

OTHER PUBLICATIONS

Yang et al., The extraction of collagen protein from pigskin, Journal of Chemical and Pharmaceutical Research, 2014, 6(2): 683-687.*
New England Tanners Club, Leather Facts, 3rd Ed., 1994, Available online at: www.bostonleather.com/assets/images/ pdf/Leather_Facts_lores.pdf.*

* cited by examiner

*Primary Examiner* — Jennifer M. H. Tichy
(74) *Attorney, Agent, or Firm* — Muncy, Geissler, Olds & Lowe, P.C.

(57) ABSTRACT

A method for preparing low endotoxin collagen is disclosed. The method includes the following steps: providing an animal skin, removing residual adipose tissues and muscle tissues, swelling the animal skin by alkaline solution, peeling the upper and lower surfaces of the animal skin, hydrolyzing the animal skin by a solution including hydrolase, salting out the low endotoxin collagen by salt solutions, and washing the low endotoxin collagen by alcohols.

8 Claims, 1 Drawing Sheet

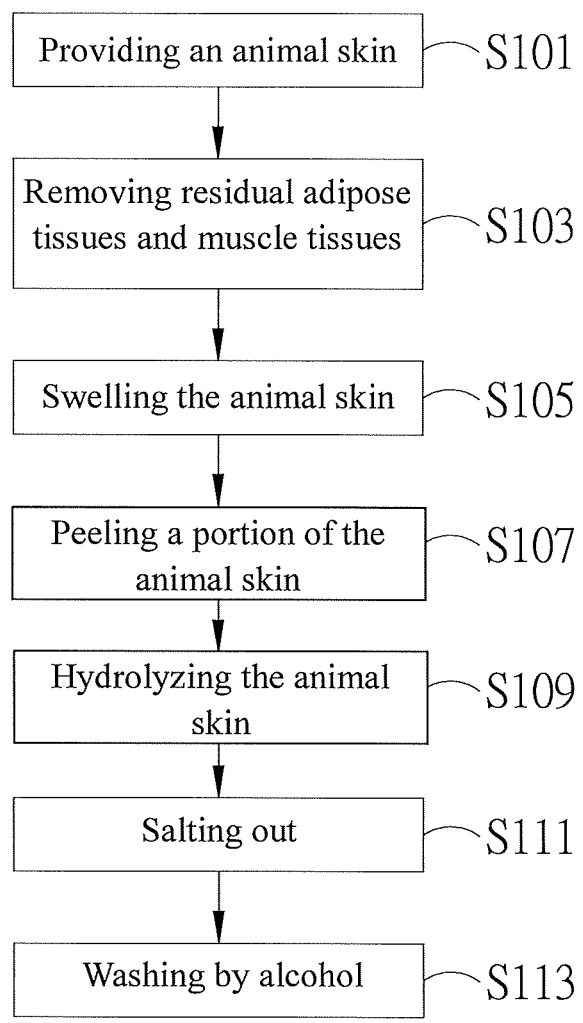

METHOD FOR PREPARING LOW ENDOTOXIN COLLAGEN

CROSS-REFERENCE TO RELATED APPLICATION

This application claims the benefit of China Patent Application No. 201710706991.9, filed on Aug. 17, 2017, in the State Intellectual Property Office of the People's Republic of China, the disclosure of which is incorporated herein in its entirety by reference.

BACKGROUND OF THE INVENTION

1. Field of the Invention

The present invention relates to a method for preparing collagen, in particular to a method for preparing low endotoxin collagen.

2. Description of the Related Art

Endotoxins refers to a component called lipopolysaccharide from Gram-negative bacteria cell walls, which will only be released in the occasion of bacterial cell death and lysis or through destruction of bacterial cells by artificial means. Lipopolysaccharide molecules are formed by three components: a specific polysaccharide, a core polysaccharide, and lipid A, with lipid A being the main toxic component. The structure of lipid A in different Gram-negative bacteria are basically similar. Therefore, despite the difference in species, infections caused by Gram-negative bacteria generally express the same endotoxin effects, which inflict clinical symptoms such as fever, leukocytosis, micro-circulatory disturbance, shock, etc. in human bodies.

In medical grade collagen industry, the amount of endotoxin determines the quality and application level of the collagen, and thus determines whether the medical grade collagen can be applied to the implantation of medical devises.

In general, the endotoxins in collagen materials are mainly from residual microbes of animal tissues, endotoxins attached on the surface of animal skin tissues, and endotoxins generated by microbial contamination during manufacturing process etc. Once the endotoxins are attached to protein or other contents, it will be extremely difficult to remove. Dry heat sterilization is commonly used to remove endotoxins on heat resistant materials, which mainly involves exposing the object for endotoxin removal under 250° C. environment for 2 hours to remove endotoxins. However, the method above cannot be applied to endotoxin removal of heat-unstable materials which decomposes under high temperature. Therefore, biopolymers such as collagen often utilize dialysis methods to remove the endotoxins in collagen solutions. The main problem of dialysis is that the viscosity of the collagen solution needs to be kept low, and therefore the solution for dialysis must be highly diluted, and then condensed after the dialysis to increase the concentration of the solution. As a result, the dialysis process can be extremely time/energy and material consuming, which greatly lowers the production capacity of low endotoxin collagen and increases production cost.

SUMMARY OF THE INVENTION

Therefore, in view of the above problems of the conventional art, it is an objective of the present invention to provide a method for preparing low endotoxin collagen through physical and chemical means.

To achieve the foregoing objective, the present invention provides a method for preparing low endotoxin collagen, including the following steps: providing an animal skin; removing residual adipose tissues and muscle tissues of the animal skin; swelling the animal skin by an alkaline solution or a buffer solution; peeling the upper and lower surfaces of the animal skin; hydrolyzing the animal skin by a solution including a hydrolase; salting out a low endotoxin collagen by a salt solution; and washing the low endotoxin collagen by an alcoholic solution.

Preferably, the step of peeling the animal skin may peel off about 0.2 mm to about 0.5 mm of the upper and lower surfaces of the animal skin.

Preferably, the hydrolase may be selected from pepsin, collagenase, chymotrypsin, peptidase, proteinase A, proteinase K, trypsin, microbial proteases, papain and any combination thereof.

Preferably, the salt solution may be selected from alkali metal phosphate solution, alkali metal halide solution and any combination thereof.

Preferably, the alcoholic solution may comprise ethanol, isopropanol and combination thereof.

Preferably, microbial growth inhibitory solution may be used in the removing step, the hydrolyzing step, the salting out step and the washing step.

Preferably, the microbial growth inhibitory solution may be selected from alcoholic solution, acidic solution, alkaline solution, high osmotic pressure solution and any combination thereof.

Preferably, the step of peeling the animal skin is performed at room temperature.

Preferably, the step of swelling the animal skin swells the animal skin in a range of 1.2 times to 2.1 times.

Preferably, the pH value of the alkaline solution or the buffer solution ranges from 11 to 13.5.

According to the above, the method for preparing low endotoxin collagen of the present invention may have the following advantages:

(1) The method of the present invention does not involve high temperature heating, so the low endotoxin collagen can be prepared without decomposing the collagen polymers.

(2) The method of the present invention can prepare low endotoxin collagen without the need of dialysis procedures, therefore also shortening the time of the manufacturing process, and also lowering the consumption of material and energy to lower the cost and increase production efficiency.

BRIEF DESCRIPTION OF THE DRAWINGS

FIG. 1 is a flow chart of the method for preparing low endotoxin collagen according to an embodiment of the present invention.

DETAILED DESCRIPTION OF THE PREFERRED EMBODIMENTS

With reference to FIG. 1, for a flow chart of the method for preparing low endotoxin collagen according to an embodiment of the present invention. As shown in FIG. 1, the method for preparing low endotoxin collagen of the present invention includes the following steps: providing an animal skin (S101); removing residual adipose tissues and muscle tissues of the animal skin (S103); swelling the animal skin (S105); peeling a portion of the animal skin (S107); hydrolyzing the animal skin (S109); salting out (S111); and washing by alcohol (S113).

In step S101, the provided animal skin can be obtained through techniques known to those of ordinary skill in the art, and obtain from vertebrates having skin systems including skin and skin derivatives, such vertebrates may include, but are not limited to, livestock or fish such as cattle, pigs, horses, sheep, chickens, ducks, turkeys, geese, whales or sharks.

In one embodiment, the provided animal skin can be subcutaneous tissues with the epidermal tissues being removed manually or mechanically.

In step S103, after removing the epidermal tissues of the animal skin, the residual adipose tissues and muscle tissues on the subcutaneous tissues may be removed manually or mechanically (for example, by fleshing machine). During the removal process of the residual adipose tissues and muscle tissues, a microbial growth inhibitory solution may be used to maintain the subcutaneous tissues in a state free from endotoxins and microbes. As such, the microbial growth inhibitory solution may be selected from the microbial growth inhibitory solution known to those of ordinary skill in the art, which may include, but are not limited to, alcoholic solution, acidic solution, alkaline solution, high osmotic pressure solution and any combination thereof.

In step S105, swelling the animal skin in a range of 1.2 times to 2.1 times by an alkaline solution. Said step can also wash away other impurities besides collagen by the alkaline solution simultaneously. The pH value of the alkaline solution ranges from 11 to 13.5. If the pH value is below 11, other impurities besides collagen cannot be washed simultaneously at this step, and cannot swell the animal skin effectively. On the other hand, if the pH value is above 13.5, protein degradation may occur and lowers the yield. Examples of the alkaline solution may include, but are not limited to, sodium carbonate, calcium hydroxide, sodium hydroxide, magnesium hydroxide, and any combination thereof. Preferably, the alkaline solution may be calcium hydroxide. In one embodiment, the alkaline solution for swelling the animal skin consists of water equaling the weight of the animal skin and 14 wt % to 16 wt % calcium hydroxide based on the weight of the animal skin.

In another embodiment, the alkaline solution may be replaced by a buffer solution having pH value ranging from 11 to 13.5. The difference between the two embodiments using alkaline solution and buffer solution is that buffer solutions have a stable pH, and no further precipitation will occur when swelling of the animal skin, thus no need to perform a conventional delimiting step, and may further simplify the process while lowering the cost. In one embodiment, the buffer solution includes phosphoric acid.

In step S107, peeling a portion of the swelled animal skin at room temperature with a splitting machine, skin planing machine or any equipment capable of peeling about 0.2 mm to about 0.5 mm of the animal skin. In order to completely remove the microbes remaining on tissue surfaces and endotoxins adhering on animal skin tissue surfaces, it is necessary to peel off the portion of animal skin exposed to the external environment, for example, peeling about 0.2 mm to about 0.5 mm of the upper and lower surfaces of the animal skin. If the peeling amount is below about 0.2 mm, microbes remaining on tissue surfaces and endotoxins adhering on animal skin tissue surfaces may not be completely removed. Considering the removal of microbes and endotoxins along with the cost of production, it is preferable to peel off about 0.2 mm to about 0.5 mm.

In step S109, performing a digestion process by a hydrolase to the animal skin after removing residual adipose tissues and muscle tissues and peeling the upper and lower surfaces to produce atelopeptide collagen. The hydrolase may include, but are not limited to, pepsin, collagenase, chymotrypsin, peptidase, proteinase A, proteinase K, trypsin, microbial proteases, papain and any combination thereof. The reaction conditions for the hydrolysis are based on the selected hydrolase. For example, when using pepsin, the hydrolysis reaction may be performed under pH value of about 1.0 to about 4.0, enzyme concentration of about 0.5 g/L to about 5.5 g/L, and stirring at a reaction temperature of 0° C. to 20° C. for 12~72 hours.

In step S111, adding a salt solution to the product of step S109 to salt out low endotoxin collagen, and washing the low endotoxin collagen with the salt solution to remove unreacted proteinase, unwanted Polysaccharides or peptides and residues of the solution used in step S109. Wherein, the salt solution may be selected from alkali metal phosphate solution, alkali metal halide solution and any combination thereof.

In step S113, washing the obtained low endotoxin collagen by an alcoholic solution and vacuum freeze to obtain collagen with high purity, high yield and low endotoxins. The alcohol may be selected from ethanol, isopropanol and any combination thereof.

The present invention will be further described in detail with the following examples.

Example 1

Remove residual adipose tissues and muscle tissues from a 4000~6000 g cow skin with epidermal tissues being removed, then swell the cow skin 1.2 times by calcium hydroxide solution (with water to calcium hydroxide ratio ranging from about 100:14 to about 100:16), and peel off 0.5 mm thickness of the upper and lower surfaces using Superzenit 3000 mm splitting machine from MOSCONI Inc.

Place the skin obtained from the previous step into 1000 to 3000 ml, 10%~20% isopropanol solution, and grind into small pieces with a meat grinder. Next, add 12~20 g pepsin, then add 480~720 ml glacial acetic acid to adjust the pH to 1.5~3.5, and stirring at 1° C. to 12° C. for 24~48 hours to obtain a mixture.

Add 3600~5700 ml sodium chloride solution to perform a salt out, and collect the precipitate after settling for 12~72 hours, then wash the obtained precipitate with 3200~4800 ml isopropanol. Vacuum freeze dry the washed precipitate at ~15~5° C. for 24~48 hours, to obtain 800~1600 g of collagen 1.

Example 2

Besides swelling the skin 2.1 times of the original volume and peeling 0.2 mm thickness from the upper and lower surfaces of the skin, other aspects of the method remain the same as Example 1, to obtain 800~1600 g of collagen 2.

Example 3

Besides swelling the skin 2.1 times of the original volume, other aspects of the method remain the same as Example 1, to obtain 800~1600 g of collagen 3.

Example 4

Besides peeling 0.2 mm thickness from the upper and lower surfaces of the skin, other aspects of the method remain the same as Example 1, to obtain 800~1600 g of collagen 4.

Comparative Example 1

Besides using 4000~6000 g cow skin without removing the adipose tissues and muscle tissues, other aspects of the method remain the same as Example 1, to obtain 650~780 g of collagen 5.

Comparative Example 2

Besides not peeling the upper and lower surfaces of the skin, other aspects of the method remain the same as Example 1, to obtain 202~443 g of collagen 6.

Comparative Example 3

Besides not swelling the skin, other aspects of the method remain the same as Example 1, to obtain 512~810 g of collagen 7.

Examine the endotoxin concentration of the collagen obtained in Examples 1~4 and Comparative examples 1~3, the results are shown below in table 1.

TABLE 1

| | Adipose tissues and muscle tissues removed | Swelling factor | Peeling thickness | Endotoxin concentration | Collagen obtained (g) | Yield (%) |
|---|---|---|---|---|---|---|
| Example 1 | ○ | 1.2 times | 0.5 mm | 2.1~7.8 eu/g | 600~900 | 15 ± 2 |
| Example 2 | ○ | 2.1 times | 0.2 mm | 2.1~8.2 eu/g | 800~1200 | 20 ± 2 |
| Example 3 | ○ | 2.1 times | 0.5 mm | 2.2~8.1 eu/g | 700~1050 | 17.5 ± 2 |
| Example 4 | ○ | 1.2 times | 0.2 mm | 2.8~8.6 eu/g | 713~1070 | 17.87 ± 2 |
| Comparative example 1 | X | 1.2 times | 0.5 mm | 650~903 eu/g | 640~960 | 16 ± 2 |
| Comparative example 2 | ○ | 1.2 times | No peeling | 782~983 eu/g | 202~300 | 5 ± 2 |
| Comparative example 3 | ○ | No swelling | 0.5 mm | 2.1~8.0 eu/g | 650~975 | 13 ± 2 |

As can be observed in table 1 above, Examples 1~4 had lower endotoxin concentration compared to Comparative examples 1 and 2, and Examples 1=4 had higher yield compared to Comparative examples 1~3. Therefore, it can be confirmed that further peeling the animal skin in an alkaline solution after removing epidermal tissues as described in the embodiments of the present invention can effectively lower the endotoxin concentration while maintaining collagen yield. In the case of the present invention which swells the animal skin by alkaline solution before peeling the surface of animal skin, since alkaline solution can also act as a microbial growth inhibitory solution, the endotoxin on the surface of the animal skin can be further reduced during the peeling process, and also suppresses endotoxin generation at said time period. Therefore, the step of swelling the animal skin can maintain low endotoxin and increase collagen yield simultaneously to avoid unnecessary loss.

As described above, the method of the present invention can prepare low endotoxin collagen without the need of high temperature heating and dialysis procedures. Therefore, low endotoxin collagen can be prepared without decomposing the collagen polymers, and be prepared with shorter process time, lower material and energy consumption, decreased production cost and increased yield.

While the exemplary embodiments of the present invention have been shown and described specifically, numerous modifications and variations could be made thereto by those skilled in the art without departing from the scope and spirit of the invention set forth in the claims.

What is claimed is:

1. A method for preparing collagen, including the following steps:
    providing an animal skin;
    removing residual adipose tissues and muscle tissues of the animal skin;
    swelling the animal skin in a range of 1.2 times to 2.1 times by an alkaline solution or a buffer solution;
    peeling off 0.2 mm to 0.5 mm of the upper and lower surfaces of the swelled animal skin;
    hydrolyzing the peeled animal skin by a solution including a hydrolase;
    salting out a collagen by a salt solution; and
    washing the collagen by an alcoholic solution.

2. The method of claim 1, wherein the hydrolase is selected from pepsin, collagenase, chymotrypsin, peptidase, proteinase A, proteinase K, trypsin, microbial proteases, papain and any combination thereof.

3. The method of claim 1, wherein the salt solution is selected from alkali metal phosphate solution, alkali metal halide solution and any combination thereof.

4. The method of claim 1, wherein the alcoholic solution includes ethanol, isopropanol and combination thereof.

5. The method of claim 1, wherein a microbial growth inhibitory solution is used in the removing step, the hydrolyzing step, the salting out step and the washing step.

6. The method of claim 5, wherein the microbial growth inhibitory solution is selected from alcoholic solution, acidic solution, alkaline solution and any combination thereof.

7. The method of claim 1, wherein the step of peeling the swelled animal skin is performed at room temperature.

8. The method of claim 1, wherein the pH value of the alkaline solution or the buffer solution ranges from 11 to 13.5.

* * * * *